United States Patent [19]

Keller

[11] Patent Number: 4,723,910

[45] Date of Patent: Feb. 9, 1988

[54] APPARATUS FOR ORTHOPEDIC AND/OR ORTHODONTIC TREATMENT

[76] Inventor: Duane C. Keller, 62 Grantwood, St. Louis, Mo. 63123

[21] Appl. No.: 635,173

[22] Filed: Jul. 27, 1984

Related U.S. Application Data

[62] Division of Ser. No. 381,379, May 24, 1982, Pat. No. 4,468,196.

[51] Int. Cl.⁴ .............................................. A61C 7/00
[52] U.S. Cl. ...................................................... 433/7
[58] Field of Search ........................... 433/5, 6, 20, 17

[56] References Cited

U.S. PATENT DOCUMENTS

| | | | |
|---|---|---|---|
| 618,105 | 1/1899 | Knapp . | |
| 646,629 | 4/1900 | Sugatt | 433/6 |
| 1,101,504 | 6/1914 | Montag | 433/17 |
| 1,207,566 | 5/1916 | Körbitz | 433/17 |
| 1,429,749 | 9/1922 | Maeulen et al. | 433/17 |
| 1,495,390 | 5/1924 | Hollingsworth | 433/71 |
| 1,773,588 | 8/1930 | Linde | 433/7 |
| 2,318,001 | 5/1943 | Linde | 433/7 |
| 2,479,780 | 8/1949 | Remensnyder | 32/17 |
| 3,327,580 | 6/1967 | Herweg | 433/6 |
| 3,478,742 | 11/1969 | Bohlmann | 128/172.1 |
| 3,837,081 | 9/1974 | Kesling | 433/6 |
| 3,925,894 | 11/1975 | Robins | 32/14 B |
| 4,055,895 | 11/1977 | Huge | 433/6 |
| 4,202,328 | 5/1980 | Sukkaire | 128/89 A |
| 4,204,326 | 5/1980 | Dimeff | 433/71 |
| 4,419,992 | 12/1983 | Chorbajian | 433/6 |
| 4,457,708 | 7/1984 | Dufour | 433/6 |

FOREIGN PATENT DOCUMENTS 568696  1/1933  Fed. Rep. of Germany ........ 433/20

*Primary Examiner*—Robert Peshock
*Attorney, Agent, or Firm*—Polster, Polster and Lucchesi

[57] ABSTRACT

Method of orthopedic and/or orthodontic treatment comprising the steps of securing bands or the like to selected teeth (e.g., selected molars) of one jaw (e.g., the upper or lower jaw) of a patient with these bands being adapted to hold an archwire. Then, the proper relationship of the mandible to the maxilla is temporarily established, such as through the use of temporary splints, allowing ligaments and muscles to function normally and maintaining the patient's proper mandibular and temporomandibular joint positions. A body of pliable, hardenable material carried by the archwire is placed in the patient's mouth with the patient's mouth open and with the archwire held in place by the bands, the body of pliable, hardenable material is in register with selected teeth (e.g., the incisors) of the patient's other arch. A buccal wire is optionally provided which contacts the outer surfaces of the front teeth and is passed distal to both the cuspids or the laterals, and is imbedded in the hardenable material on the inside of the selected teeth (e.g., front incisors and cuspids). Then, the patient closes his mouth so that with the mandible and temporomandibular joints properly positioned with respect to the maxilla, the selected teeth of the other jaw form an impression in the body of hardenable material such that after hardening of the material and after the temporary splints are removed, the impression formed in the body of the hardenable material by the selected teeth of the other jaw serves as a reference to stabilize the position of the mandible, maxilla and temporomandibular joints during an extended period of orthopedic and orthodontic treatment whereby the patient's teeth may be orthodontically moved to their optimal anatomical and physiological positions with the mandible and temporomandibular joints held in their proper position.

Apparatus for carrying out the above-described method is also disclosed.

10 Claims, 6 Drawing Figures

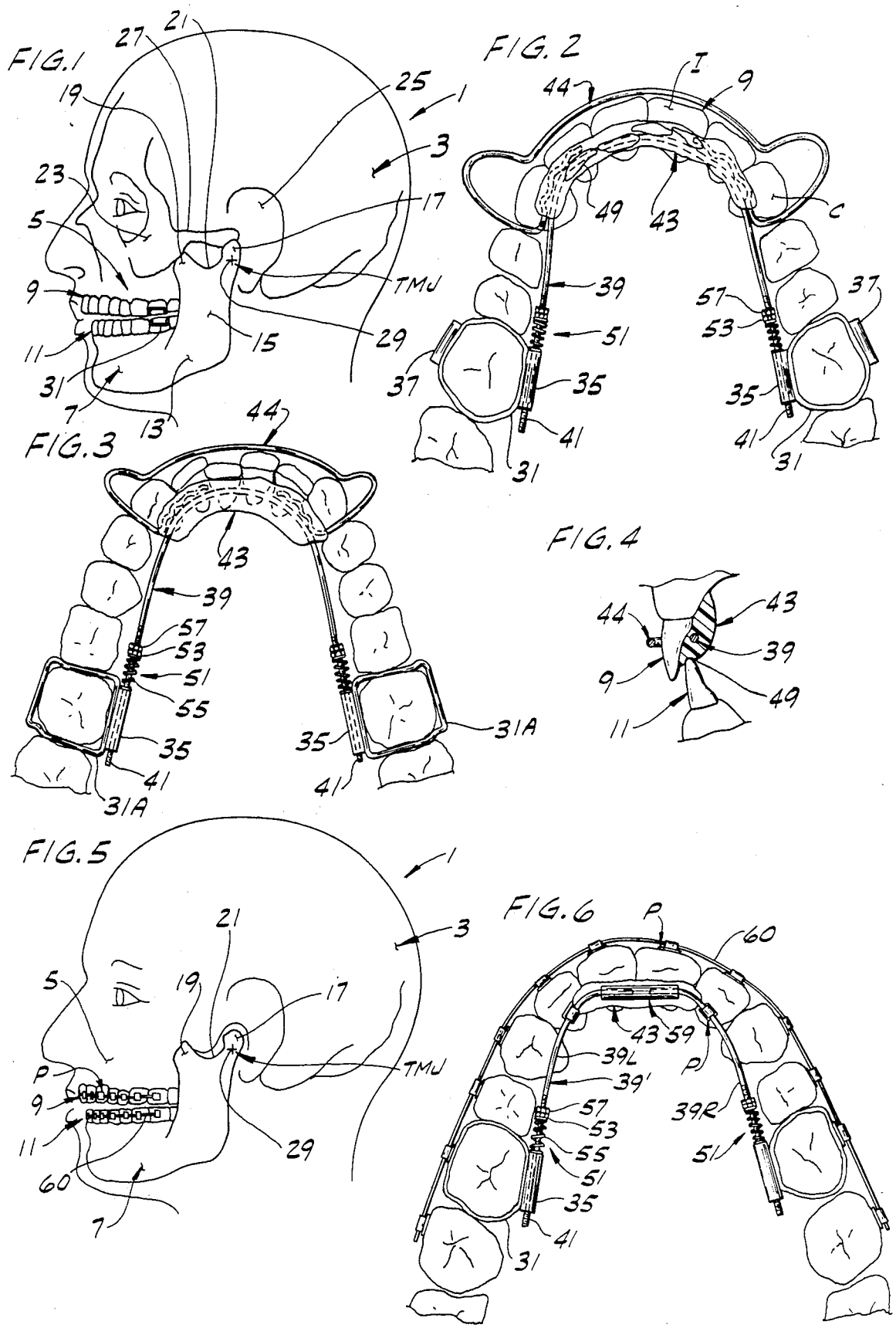

APPARATUS FOR ORTHOPEDIC AND/OR ORTHODONTIC TREATMENT

This is a division of application Ser. No. 381,379, filed May 24, 1982, and now U.S. Pat. No. 4,468,196 issued 8/28/84.

BACKGROUND OF THE INVENTION

This invention relates to a method of and apparatus for the orthopedic and/or orthodontic treatment of a patient's temporomandibular joints, mandible, maxilla and the teeth carried thereby and of the patient's muscles of mastication, ligaments and skeletal features constituting the masticatory system in which the proper positions of the mandible and temporomandibular joints are established with respect to the maxilla and in which the teeth are, over an extended period of time, moved to their desired locations utilizing the proper position of the mandible, maxilla, and temporomandibular joints as a reference so that after treatment, not only are the teeth properly positioned, but the position of the mandible, maxilla and temporomandibular joints are properly orthopedically established and stabilized.

Oftentimes in orthodontic treatment, the patient's teeth are moved relative to one another so as to correct many different problems. Some of these problems may include overbite, overject, protruded or intruded teeth, rotated teeth, missing teeth, teeth that are maloccluded or that have not properly erupted, and teeth which are angularly displaced because insufficient room is available in the patient's jaw. Generally, after orthodontic treatment, it is desirable that the patient's teeth be cosmetically or aesthetically aligned However, in actual practice, it has been found that many times after extensive conventional orthodontic treatment, patients sometimes have aesthetically aligned teeth, but the proper anatomical relationship of the mandible, maxilla, temporomandibular joints, muscles of mastication, ligaments and skeletal elements constituting the masticatory system is not properly established. Without this proper anatomical relationship properly established and stabilized, many well-known problems, including malocclusion, difficulty in chewing, severe headaches, neck aches, backaches, ear problems (tinnitis), jaw pain, and facial pain can be traced to the improper anatomical positioning of the mandible, maxilla, muscles of mastication and temporomandibular joints. In severe cases, this can result in certain forms of degenerative arthritis of the temporomandibular joint, and can lead to and be associated with improper positioning of the tongue and loss of oral muscle strength resulting in deviate swallowing.

In general, the correction of a patient's deviate swallow is referred to as myofunctional therapy. More particularly, myofunctional therapy relates to the selective training, positioning, and strengthening of specific muscles or groups of muscles used in speech, mastication, deglutition and swallowing, particularly to the selective training of the tongue.

In general, the prior art orthodontic treatment methods and appliances teach the concept of attaching various bands, brackets, and other appliances to the teeth or to the patient's head and applying corrective orthodontic forces to selected teeth such that these selected teeth are moved within the patient's jaw thus straightening the teeth or providing room for other teeth thus establishing a desired relationship between all of the teeth in the person's mouth. However, as mentioned, oftentimes these prior art orthodontic appliances and methods did not utilize the desired position of the mandible, maxilla, muscles of mastication, and temporomandibular joints as a reference point. Additionally, many prior art appliances were cumbersome and could not readily be removed or adjusted either by the dentist, orthodontist or by the patient.

Still further, prior art orthodontic treatment methods and appliances did not, for the most part, incorporate a simultaneous orthopedic treatment which not only resulted in the desired orthodontic results, but also resulted in orthopedic stabilization of the mandible, maxilla, muscles of mastication, and the tempomandibular joints. Likewise, the prior art orthodontic treatments did not address myofunctional swallowing impairments oftentimes associated with the above-described orthodontic and orthopedic problems.

Thus, there has been a longstanding need for a method of combined orthopedic and orthodontic treatment and apparatus for carrying out the method in which the proper relationship of the mandible, maxilla, muscles of mastication and the temporomandibular joints are utilized as a reference during the entire course of orthodontic treatment such that the teeth may be orthodontically moved to their desired positions with respect to the proper or normal anatomical positions of the mandible, maxilla, muscles of mastication and the temporomandibular joints, and in which swallowing myofunctional therapy could be simultaneously given to the patient.

Reference may be made to such U.S. Pat. Nos. 618,105, 1,101,504, 1,207,566, 1,429,749, 1,773,588, 2,479,780, 3,327,580, 3,478,742, 3,925,894 and 4,202,328 which describe prior art orthodontic treatments and apparatus in the same general field as the present invention.

SUMMARY OF THE INVENTION

Among the many objects and features of this invention may be noted the provision of a method of orthopedic and/or orthodontic treatment and apparatus for carrying out this treatment method which allows mandible positioning and which allows the teeth to be moved relative to a properly established anatomical reference;

The provision of such a method and apparatus which, by utilizing the proper mandible, maxilla, temporomandibular joint relationship as a reference, optimizes muscle function, improves the aesthetics of the orthodontic treatment, improves chewing action, and, after treatment, results in a masticatory system which is stable;

The provision of such a method of treatment and apparatus which is useful in myofunctional therapy;

The provision of such a treatment method and apparatus which allows multiple orthodontic treatments to proceed at the same time;

The provision of such a treatment method and apparatus which permits maximum flexibility for the treating dentist or orthodontist and which eases placement of archwires and other orthodontic appliances;

The provision of such orthodontic apparatus in which at least certain parts of the apparatus are readily removable by the patient for increased aesthetic purposes and for cleanability purposes;

The provision of such an orthodontic method and apparatus which is useful in orthodontically treating partially erupted or super-erupted teeth;

The provision of such an orthodontic method which is useful in oral surgery to serve as a reference for a surgically re-located mandible or maxilla;

The provision of such apparatus which allows for adjustment of the apparatus by the patient in accordance with a pre-established schedule thus speeding orthodontic treatment and minimizing the number of visits the patient must make to the orthodontist's office;

The provision of such a treatment method and apparatus which allows normal development of both arch forms, which allows normal eruption of the patient's teeth to their fullest genetic potential, and which allows normal alveolar and condylar bone growth;

The provision of such a treatment method and apparatus which results in normal orthopedic position of the mandible, maxilla and temporomandibular joints thereby allowing optimal masticatory muscle function;

The provision of such a treatment method and apparatus which permits the arch expansion and distilizing of posterior teeth; and anterior movement of the front teeth;

The provision of such a treatment method in which, after completion of the primary orthodontic treatment, certain of the components can be used as a temporary retainer;

The provision of such a treatment method and apparatus which facilitate alveolar and condylar bone growth; and The provision of such a treatment method and apparatus which is easy to install, which is comfortable to the patient, and which is of relatively uncomplicated construction.

Other objects and features will be in part apparent and in part pointed out hereinafter.

Briefly stated, the method of this invention of orthopedic and/or orthodontic treatment comprises the steps of securing means (e.g., bands) to selected teeth (e.g., to certain of the molars) to one jaw of a patient (e.g , the upper jaw) with these securing means being adapted to hold an archwire in position. Then, the proper relationship of the patient's mandible and temporomandibular joints is temporarily established, as, for example, by utilizing conventional splints. A body of pliable, hardenable material (e.g., an acrylic plastic or the like) carried by the archwire is positioned such that the body of hardenable material is held in place within the patient's mouth in register with selected teeth of the patient's jaw (e.g., in register with the incisors of the patient's upper jaw). A second wire is optionally placed buccal to the front teeth, turned distal to the cuspids or laterals, and imbedded in the hardenable plastic. This optional buccal wire serves to maintain the anterior position archwire and bitepiece so they do not place undue occlusal or orthodontic forces on the teeth and so that archwire and bitepiece may be more readily inserted and removed. Then, the patient closes his mouth so that with the mandible and temporomandibular joints properly positioned, the selected teeth of the other jaw (e.g., the lower incisors) form an impression in the body of the hardenable material whereby after hardening of the body of material and after removal of the means used for temporarily establishing the mandible and temporomandibular joints, the impressions formed in the body of hardenable material by the selected teeth of the other jaw serve as a reference to stabilize the position of the mandible and temporomandibular joints during an extended period of treatment whereby the patient's teeth may be moved to their respective desired positions with the mandible and temporomandibular joints held in their proper anatomical positions.

Apparatus for carrying out the above-described treatment includes means, such as bands or the like, which are secured to selected teeth (e.g., the molars) on one jaw of the patient (e.g., the upper jaw). These bands include means for receiving and holding an archwire. A body of pliable, hardenable material is carried by and is held in place on the archwire with the body of hardenable material being generally in register with selected teeth of the patient's jaw (e.g., in register with the incisors of the upper jaw). A reinforcement wire is optionally placed buccal to the front teeth, turned distal to the cuspids and imbedded in the hardenable material. Thus, when the patient closes his mouth, the selected teeth of the other jaw form an impression in the body of hardenable material such that after the material has hardened, the impressions formed therein establish a reference holding the mandible and temporomandibular joints in their desired positions, even after temporary means (e.g., the splints) have been removed. Thus, this body of hardenable material (referred to as a bitepiece) with the tooth impressions formed therein serves as a reference for establishing the proper anatomical position of the mandible and temporomandibular joints throughout the entire course of the orthodontic treatment whereby various teeth in the patient's mouth may be moved to their desired locations utilizing the proper anatomical position of the mandible, maxilla, muscles of mastication, and the temporomandibular joints as a reference.

BRIEF DESCRIPTION OF THE DRAWINGS

FIG. 1 is a left side elevational view of a typical patient's head prior to treatment illustrating the main anatomical and skeletal features of the patient's head and jaw with the apparatus of the present invention installed on the patient's teeth;

FIG. 2 is a view taken along line 2—2 illustrating the teeth of the upper jaw of the patient shown in FIG. 1 with an appliance of the present invention installed on the upper teeth and illustrating the method of treatment of the present invention;

FIG. 3 is a view taken along line 3—3 of FIG. 1 illustrating the patient's lower teeth with apparatus of the present invention installed thereon for treatment of the patient's teeth in accordance with this invention;

FIG. 4 is a view taken generally along line 4—4 of FIG. 2 showing patient's jaw and illustrating the appliance of FIG. 2 installed on the teeth of the upper arch and illustrating the teeth of both the upper and lower jaws in engagement with the bitepiece with the bite piece of the present invention serving as a reference for holding the mandible, maxilla, and temporomandibular joints in a predetermined anatomical relationship;

FIG. 5 is a view similar to FIG. 1 after or during treatment with additional orthodontic appliances of the present invention installed on the patient's teeth for orthodontic treatment; and FIG. 6 is a view similar to FIG. 2 taken along line 6—6 of FIG. 5 showing further orthodontic treatment apparatus of the present invention;

Corresponding reference characters indicate corresponding parts throughout the several views of the drawings.

DESCRIPTION OF PREFERRED EMBODIMENTS

Referring now to the drawings, and more particularly to FIG. 1, the head, as generally indicated at 1, of a patient is illustrated. The head, of course, includes a skull 3 which may be divided into two main sections or parts, viz , the cranium and the skeleton of the face. A brief description of the various bones which comprise both the cranium and the skeleton of the face, as they relate to the method and apparatus of the present invention will now be described. Specifically, the skeleton of the face includes the maxilla 5 in which the teeth of the upper jaw are embedded and the mandible 7 in which the teeth of the lower jaw are embedded. The upper teeth are generally indicated by reference character 9 while the lower teeth are generally indicated by reference character 11.

Mandible 7 includes a body (corpus mandibulae) 13. The body of the mandible is curved (when viewed in plan) with a ramus portion 15 (ramus mandibulae) projecting upwardly at each end. At the upper rear of the ramus, the condyle projection 17 is formed, and at the upper front end of the ramus, the coronoid process 19 is formed. A so-called mandibular notch 21 arches downwardly between condyle 17 and coronoid process 19.

The cranium portion of the skull includes the zygomatic bones 23 which form the outer portion of the eye socket and which are generally known as the cheekbones. In addition, the cranium, immediately above the location of the ear, includes a temporal bone 25. As indicated at 27, a zygomatic arch bridges between the posterior end of the maxilla bone in the lower portion of the temporal bones on each side of the head. The condyle projection 17 of mandible 7 is generally socketed in the glenoid fossa of the temporal bone 25 and the coronoid process 19 of the mandible fits behind zygomatic bone 23 in the glenoid fossa.

Generally, the temporomandibular joint, as generally indicated at TMJ, connects the rear of mandible 7 with the cranium and is a combined ginglymus and gliding point. Generally, the temporomandibular joint TMJ is comprised of a number of ligaments (not shown) including the articular capsule ligament, the lateral ligament, the sphenomandibular ligament, the articular disk, and the stylomandibular ligament. The articulation of mandible 7 includes the opening and closing of the jaws, the protrusion in fore and aft directions of the mandible, and lateral displacement of the mandible. Generally, there are two parts to this articulation, one between the condyle and the articular disk (not shown) and between the disk and the glenoid fossa. When the jaws are opened and closed utilizing the muscles of mastication (not shown), motion takes place on both parts, the disk glides anteriorly on the articular tubercle or eminence (not shown), and the condyle process 17 moves on the disk like a hinge, causing the mandible to rotate about a center of suspension, as indicated at 29, near the center of the condyle process. This is a somewhat movable center of suspension and is defined by the attachment of the sphenomandibular ligament to the lingula (also not shown), and by a sling formed by the masseter and the pterygoideus medialis. When the jaws are open, the angle of the mandible moves posteriorly while the condyle process 17 glides forwardly along the emmenentia of the anterior tubercle as the short arm of a lever, and the chin, as the long arm of the lever, describes a wide arc. The motion between the condyle process and the articular disk is largely one of accommodation to this change in position. When the jaws are closed, some of the force is applied to the condyle process as a fulcrum, especially in biting with the incisors, but in chewing with the molars, the pressure comes more directly between the teeth and the condyle process acts as a glide more than as a fulcrum. In grinding or chewing movement of the mandible, there is a lateral displacement of the mandible caused by a forward movement of the condyle process and then the mandible is brought back into place by the action of the closing muscles and the meshing of the teeth. The condyle process 17 of the mandible 7 may be displaced alternately, or the same one may be displaced repeatedly as in chewing with one side of the mouth.

As is well known, it is imperative that, in order to establish a proper bite and chewing action, the relative positions of mandible 7, maxilla 9, the above-described bones and ligaments of the cranium and the associated primary and secondary muscles of mastication be in their proper anatomical relationship. It is an object of this invention that, before orthodontic treatment begins, the proper relationship of the mandible 7, maxilla 9, and temporomandibular joints be properly orthopedically established and be used as a reference throughout the course of treatment whereby not only are the teeth orthodontically moved to their desired positions, but the mandible and maxilla are orthopedically moved to their respective proper anatomical positions, the proper bite is established, the proper positions of the mastication muscles are established, and the proper positions of the temporomandibular joints are established and stabilized.

Referring now particularly to FIGS. 2 and 3, apparatus of the present invention for carrying out the method of this invention for orthopedic and/or orthodontic treatment will now be described in detail. As indicated generally at 31, bands or other appliances (such as an Adam's clasp 31A, see FIG. 3) may be secured to selected teeth (e.g., selected molars) on opposite sides of one of the patient's jaws (i.e , either the upper or the lower jaw). Each band 31 includes an inside tube 35 facing generally in fore and aft direction. An outside tube 37 may be optionally carried by bands 31. An archwire, as generally indicated at 39, is fitted in the patient's mouth so as to be on the inside or lingual surfaces of the teeth. As indicated at 41, the free ends of archwire 39 are threaded and the threaded ends of the archwire are received within inside tubes 35 provided on bands 31. Thus, these tubes constitute means for receiving and holding the archwire. Optionally, tubes 35 may be pivotally secured to bands 31 so as to permit the tubes and the archwire received therein to pivot about a horizontal axis to aid in alignment of the archwire relative to the teeth.

Further in accordance with this invention, a body 43 of formable, hardenable material, such as acrylic plastic or the like, as shown in FIG. 3, is applied to and carried by the front or center portion of archwire 39 so as to form an impression of the inside or lingual faces of the selected teeth of the one jaw (e.g., the incisors I and the canine teeth C of the patient's upper jaw). An optional buccal holding or bracing wire 44 is placed in contact with the buccal or outer surfaces of the front teeth. This wire is bent distal to the cuspid or laterals and is imbedded in the hardenable acrylic. This wire 44 serves to support the appliance in the mouth, aids in guidance and prevents any flaring of the anterior teeth, and aids in removal and insertion of arch wire 39. Further, optional buccal wire 44 may be formed so as to exert a resilient or spring force on bitepiece 43 so as to more positively hold the bitepiece in position on the selected lingual surfaces of the teeth throughout the course of treatment, even if archwire 39 would inadvertently be bent.

With the patient's mandible and temporomandibular joints TMJ properly established in the conventional manner, such as by using splints between the rear molars as required, the patient is then instructed to close his mouth so that selected teeth in the other jaw (e.g., the incisors of the lower jaw) move into engagement with the body of hardenable material or bitepiece 43 on archwire 39 behind the incisors of the upper jaw thereby to form an impression 49 therein. Upon hardening, the body 43 of hardenable material forms a so-called bite piece which conforms not only to the lingual or inside surfaces of the upper incisors, but also has an impression 49 formed therein of the incisors of the opposite or lower jaw. It will be appreciated that with the temporary splints removed from between the patient's molars and with the patient's lower incisors fitted into impressions 49 formed in bite piece 43, the mandible and temporomandibular joints TMJ are thus positively held in their preferred anatomical positions. Thus, in accordance with the method and apparatus of this invention, bite piece 43 carried by archwire 39 serves as a reference point throughout the entire course of orthodontic treatment of the patient for maintaining the mandible and temporomandibular joints in their proper orthopedic positions and providing a reference to which the patient's teeth may be orthodontically moved so that after orthodontic treatment, not only are the teeth orthodontically moved to their desired locations, but the bite of the patient is established so as to maintain the proper orthopedic position of the mandible and temporomandibular joints, even after removal of all orthodontic appliances.

Further in accordance with this invention, the shape of bitepiece 43, particularly the rear or anterior portions thereof, may be shaped to fit into the patient's mouth so as to serve a guide for the tongue aiding in myofunctional therapy thus aiding and correcting any swallowing difficulties that the patient may have. More particularly, the curvature of the threaded arch wire 39 posteriorly of bite piece 31 and the shape of the lingual tubes 35 carried by bands 31 serve as a guide for placement of the tongue against the maxilla (i.e., the hard palate) and against the soft palate thus aiding normal swallowing actions. The lingual or inside tubes 35, the shape of arch wire 39, and the upper and lingual surfaces of bite piece 43 serve as guides and physical reminders to the patient so as to prevent placement of the tongue against the teeth and so as to properly position the tongue within the mouth for proper swallowing. Thus, arch wire 39 and bite piece 43 may serve the dual function of not only establishing a reference point for orthopedic and/or orthodontic treatment in which the temporomandibular joint is held in its desired position, but it also may serve as a myofunctional therapy mouthpiece.

As generally indicated by reference 51, means may be installed in the patient's mouth for applying desired orthodontic forces to selected of the patient's teeth so as to move these selected teeth for desired orthodontic purposes. Specifically, arch wire 39 may be utilized to apply forces to the teeth which may be utilized to expand or contract the arch of the teeth. An adjustment nut 53 may be threaded onto the threaded ends 41 of arch wire 39 and a compression coil spring 55 is interposed between tube 35 carried by band 31 and the adjustment nut so that the spring exerts a forwardly directed force on the adjustment nut and on the arch wire and a distillizing force on the molars to which bands 31 are attached. These forces tend to expand the arch and to distilize the posterior teeth. Also, a stop nut 57 may be threaded on the threaded ends 41 of the arch wire and with adjustment nut 53 in its desired position so that spring 55 exerts a predetermined amount of force, the stop nut may be tightened against the adjustment nut thereby locking both nuts in their desired position and thus maintaining the desired force on the arch wire. It will be appreciated that the patient may readily reach into his mouth and grasp the front portion of the arch wire and, by pulling it forwardly, the ends of the arch wire will slip free of inside tubes 35 thus permitting the removal of the arch wire and the bitepiece for cleaning or for aesthetic reasons. With springs 53 in place on the ends of the arch wire, the patient may readily re-insert the ends of the arch wire and, because of the lingual impressions of the front teeth formed on the bite piece 43 and the buccal bracing wire 44, the arch wire may be readily re-installed in its predetermined position in the mouth and the pre-adjusted orthodontic forces will automatically be re-applied to the teeth. Of course, by periodically adjusting the position of adjustment nuts 53, springs 55 may be progressively compressed thereby to increase the amount of force applied to the teeth. Thus, a predetermined adjustment schedule may be prearranged by the dentist or orthodontist (e.g., the progressive adjustment of nuts 53 and 57 and the periodic changing of springs 55) may be given by the dentist or orthodontist to the patient thus reducing the need for office visits.

Alternatively, adjustment nuts 53 and stop nuts 57 may be provided on the rear of the threaded ends of the inner arch wire behind tube 35 with the spring interposed between the adjustment nut and the rear end of the tube so that the arch wire is retracted rearwardly thus moving the posterior teeth forwardly.

As in conventional orthodontic practice, various pads or brackets may be adhesively bonded to the inside or outside of the patient's teeth, generally as indicated at P in FIG. 6, and connected to the inner archwire 39 so that a correcting force may be applied to the teeth to form the arch.

Further in accordance with this invention, inner arch wire 39' may be formed in two parts, as indicated at 39R, 39L in FIG. 6 with threads formed on the inner ends thereof. The inner threads of threaded portions 39R are right-hand threads while the threads on portion 39L are left-hand threads. These threaded inner ends of the inner arch wire are threadably received in a barrel member 59 which has corresponding right and left-hand threaded openings therein so that the barrel together with the inner ends of the arch wire constitute a turn buckle assembly. Thus, upon rotating barrel 59, the inner arch wire 39' may be selectively expanded or contracted independently of springs 55.

Additionally, an outer (buccal) arch wire 60 is received in outer tubes 37 on bands 31 and is fitted to the teeth with the outer arch wire received in various pads brackets or bonds P bonded or cemented to the outside (buccal) faces of the teeth. In the conventional and well-known manner, these inner and outer arch wires 39', 60 and the brackets may be utilized with various springs and elastomeric orthodontic appliances to apply whatever forces are required to orthodontically treat the patient's teeth. A detailed description of the various orthodontic force applying apparatus and techniques is not herein required because these are well-known to those skilled in the art.

Specifically, referring to the method of orthodontic treatment of the present invention, reference may be made to FIGS. 1-4 of the drawings. Generally, the treating dentist or orthodontist will affix a pair of bands 31 to selected rear molars in the patient's mouth, for example to the rear molars of the upper jaw as indicated in FIG. 2. Then, the proper positions of the mandible, maxilla, and the temporomandibular joints are established utilizing temporary splints (or other suitable means) which are fitted between the upper and lower molars in the conventional manner so that the position of the condyle 17 and the coronoid process 19 and the body of the mandible 7 are in proper anatomical relationship with the glenoid fossa of the temporal plate 25 and maxilla 5.

Generally, these splints are hard acrylic orthodontic appliances specifically fabricated to fit over the upper or lower teeth. These splints may be reinforced with bent metal wires. The acrylic portion of the splint is made to fit over the teeth of the selected arch (i.e., the upper or lower molars) and may be attached to the teeth by means of conventional orthodontic clasps or wires. A soft acrylic layer is typically added to the outer surfaces of the splints. The teeth are then closed together so that the opposing teeth form an impression in the soft acrylic layer on the splints. The opposing arch is positioned relative to the splints applied to the selected teeth of the other arch so that the mandible and temporomandibular joints are in proper anatomical and physiological position with respect to the maxilla (the base of the cranium). The acrylic surfaces on the splints are then allowed to set up or harden so that the teeth have a permanent place therein in which they may interdigitate. The acrylic is adjusted to allow proper freedom of movement of all lateral and protrusive jaw movements. Sometimes, guidance planes may be built into the splints to aid these lateral or protrusive movements. This relative position of the parts of the patient's cranium and jaw is maintained until an improvement of a symptom, such as headache, neck aches, backaches, muscle spasms, reduction of jaw locking pain, difficulty in swallowing, clicking or popping noises in the tempomandibular joints, noise in the ears, or an improvement of postural changes associated in normal opening, closing, and sidewise movement of the mandible are observed. It has been observed that with the mandible, the maxilla, and the temporomandibular joints properly anatomically positioned, certain of the above-mentioned symptoms will improve. This is an indication that the masticatory system is in its proper anatomical position. Further, with the mandible and temporomandibular joints properly positioned, the ligaments that hold the cartilaginous disk between the glenoid fossa and the head of the condyle projection may return to their normal anatomical lengths and positions.

With the position of the mandible and temporomandibular joints temporarily positioned by the splints, as described above, arch wire 39 with the pliable bite piece 43 installed thereon is fitted in the patient's mouth and the forward face of the bite piece 43 is impressed against the inner or lingual faces of the incisors and canine teeth of the upper jaw. Thus, an impression of the lingual surfaces of these teeth are formed in the bite piece. Buccal wire 44 is placed to contact the outer surface of the anterior teeth, is contoured to bend toward and is embedded into the hardening acrylic. Then, the patient is instructed to close his jaws until the rear molars come in contact with splints thus properly positioning the mandible and temporomandibular joints and simultaneously forming indentations 49 in the lower face of the bite piece by the incisors and canine teeth of the opposite or lower jaw. Upon hardening of the bite piece material, the temporary splints S may be removed and upon the patient closing his mouth, the bite piece 43 fits snugly against the lingual surfaces of the selected teeth of the upper jaw and receive the selected teeth (e.g., the incisors and possibly canine teeth) of the opposite (lower) jaw thereby to hold the mandible and temporomandibular joints TMJ in their proper anatomical positions. Thus, throughout the course of orthopedic and-/or orthodontic treatment method of the present invention, which may require an extended period of time (e.g., many months), bite piece 43 serves as a permanent reference between the patient's mandible, maxilla, teeth and temporomandibular joints. As orthopedic and/or orthodontic forces are applied to the teeth to move them to their proper and desired positions, the teeth are moved not only so as to be cosmetically correct, but also so as to establish a proper bite when the temporomandibular joints and the mandible are in their proper anatomical positions. At the end of the treatment, not only are the patient's teeth orthodontically aligned, but the mandible, maxilla and temporomandibular joints are orthopedically stabilized in their proper positions.

Referring to FIG. 3, the orthodontic apparatus of the present invention may be alternatively fitted to the lower teeth 11 in the manner above-described and may be utilized in accordance with the above-described orthodontic treatment method.

As utilized throughout the above disclosure of the orthopedic and/or orthodontic method of treatment and apparatus of the present invention, the term "temporomandibular joint" is defined to include not only the specific portions of the mandible and cranium skeletal structure together with the associated ligaments as heretofore described, but also to include the proper positions of the mandible and the maxilla. Thus, throughout this specification and the following claims, when it is stated that in accordance with this invention one establishes the proper relationship of the patient's temporomandibular joints, it will be understood that not only is the center of suspension of the joint, as indicated at 29 in FIG. 1 is properly positioned, but also that the disappearance of one or more of the symptoms heretofore described oftentimes associated with improperly positioned temporomandibular joints may be dissipated or improved. Thus, it is expressly intended that in this specification that the term "temporomandibular joint" shall be interpreted in a broad and not a limiting manner.

In view of the above, it will be seen that the other objects of this invention are achieved and other advantageous results obtained.

As various changes could be made in the above constructions or methods without departing from the scope of the invention, it is intended that all matter contained in the above description or shown in the accompanying drawings shall be interpreted as illustrative and not in a limiting sense.

What is claimed is:

1. Apparatus for the orthodontic and orthopedic treatment of a patient comprising securing means applied to selected teeth of one jaw of a patient, an archwire carried by said securing means and being carried by said securing means, temporary removable means for temporarily, fixedly establishing the proper relation of at least one of the patient's temporomandibular joints, means carried by said archwire serving as a reference throughout the course of the treatment for properly establishing the position of said at least one of the patient's temporomandibular joints, said reference means comprising a body of pliable, hardenable material carried by said archwire so that said body of pliable, hardenable material is generally in register with selected teeth of the patient's other jaw such that when the patient closes his mouth with the position of said at least one temporomandibular joint so temporarily, fixedly established, said other selected teeth of said other jaw form an impression in said body of pliable material such that after hardening of the pliable material and after removal of said temporary, removable means for temporarily, fixedly establishing the position of the temporomandibular joint, said archwire and said body of hardened material carried thereby remain in place within the patient's mouth for receiving said selected teeth of the other jaw in their respective impressions in said body thereby to maintain said at least one temporomandibular joint in its proper relation for serving as said reference through the course of treatment and for permitting chewing without substantial interference with said apparatus.

2. Apparatus as set forth in claim 1 wherein said securing means further comprises a tube and wherein said arch wire is removably received within said tube so that said arch wire together with said bite piece affixed thereto may be readily removed from and installed in the patient's mouth by the patient.

3. Apparatus as set forth in claim 2 wherein the ends of said arch wire are threaded and wherein said apparatus further comprises a compression coil spring installed on said arch wire and an adjustment nut threadably received on arch wire whereby with the arch wire installed in said tubes and with said bite piece in engagement with the lingual surface of said selected teeth, said spring serves to apply a force to at least selected teeth of said patient's one jaw.

4. Apparatus as set forth in claim 3 further comprising means for adjustment of force applied to the patient's teeth via said arch wire.

5. Apparatus as set forth in claim 4 wherein said arch wire includes a turnbuckle comprising a first portion of said arch wire having first threads thereon, a second portion of said arch wire having second threads thereon, and a barrel for threadably receiving said first and second threaded portions, the threads on said first and second portions being in opposite directions so that upon turning said barrel in one direction or another, said arch wire may be expanded or contracted.

6. Apparatus as set forth in claim 3 wherein said tubes are pivotally secured to said securing means whereby said tubes together with the archwire installed therein are free to pivot about a generally horizontal axis thereby to aid in alignment of the archwire with respect to the patient's teeth.

7. Apparatus as set forth in claim 1 wherein said archwire carrying said body of pliable, hardenable material constitutes a lignual archwire, and wherein said apparatus further includes a buccal archwire operatively engageable with at least certain of the patient's teeth for applying desired orthodontic forces to the patient's teeth.

8. Apparatus for the orthodontic and orthopedic treatment of a patient comprising securing means secured applied to selected teeth of one jaw of a patient, an archwire carried by said securing means, and being removably secured to carried by said securing means, temporary removable means for temporarily, fixedly establishing the proper relation of at least one of the patient's temporomandibular joints, means carried by said archwire for serving as a reference throughout the course of the treatment for properly establishing the position of said at least one of the patient's temporomandibular joints, said reference means comprising a body of pliable, hardenable material carried by said archwire so that said body of pliable, hardenable material is generally in register with selected teeth of the patient's other jaw such that when the patient closes his mouth with the position of said at least one temporomanidbular joint so temporarily, fixedly established, said other selected teeth of said other jaw form an impression in said body of pliable material such that after hardening of the pliable material and after removal of said temporary, removable means for temporarily, fixedly establishing the position of the temporomandibular joint, said archwire and said body of hardened material carried thereby remain in place within the patient's mouth for receiving said selected teeth of the other jaw in their respective impressions in said body thereby to maintain said at least on one temporomandibular joint in its proper relation for serving as said reference throughout the course of treatment and for permitting chewing without substantial interference with said apparatus, said archwire and said body of material being disposed on the lingual side of preselected teeth of said one jaw, said body of material being referred to as a bit piece, and wherein a portion of said bite piece adjacent said pre-selected teeth of the one jaw on which said securing means are fastened has an impression formed therein corresponding to the lingual surfaces of said selected teeth of said one jaw adjacent said bite piece so that these lingual impressions aid in locating the bite piece.

9. Apparatus as set forth in claim 8 further comprising a buccal wire being at least in part inserted into said hardenable material of said bite piece and being engageable with the buccal surface of said pre-selected teeth of said one jaw thereby to aid in holding said bite piece in engagement with the lingual surfaces of said pre-selected teeth.

10. Apparatus as set forth in claim 8 wherein the anterior surface of said bite piece is so structured to form a guide for patient's tongue thereby to aid in myofunctional therapy whereby the bite piece serves both as a reference for establishing the proper temporomandiular joint position and as a myofunctional treatment appliance.

* * * * *